US010571169B2

(12) United States Patent
Haack et al.

(10) Patent No.: US 10,571,169 B2
(45) Date of Patent: Feb. 25, 2020

(54) TEST CHAMBER WITH TEMPERATURE CONTROL DEVICE

(71) Applicant: WEISS UMWELTTECHNIK GMBH, Reiskirchen (DE)

(72) Inventors: Christian Haack, Marburg (DE); Johannes Teichmann, Geislingen (DE)

(73) Assignee: WEISS UMWELTTECHNIK, Reiskirchen (DE)

( * ) Notice: Subject to any disclaimer, the term of this patent is extended or adjusted under 35 U.S.C. 154(b) by 223 days.

(21) Appl. No.: 15/795,459

(22) Filed: Oct. 27, 2017

(65) Prior Publication Data
US 2018/0120003 A1 May 3, 2018

(30) Foreign Application Priority Data

Nov. 1, 2016 (EP) .................................. 16196746

(51) Int. Cl.
*F25B 7/00* (2006.01)
*F25B 27/02* (2006.01)
(Continued)

(52) U.S. Cl.
CPC ............... *F25B 40/02* (2013.01); *F25B 7/00* (2013.01); *F25B 15/00* (2013.01); *F25B 21/02* (2013.01);
(Continued)

(58) Field of Classification Search
CPC .. F25B 7/00; F25B 21/02; F25B 27/02; F25B 40/02; F25B 40/04; F25B 2400/05; F25B 2400/054; F25B 2600/2501
See application file for complete search history.

(56) References Cited

U.S. PATENT DOCUMENTS 3,487,653 A * 1/1970 Myre ...................... F25B 9/006
62/76
5,724,832 A * 3/1998 Little ....................... B01D 8/00
62/114

FOREIGN PATENT DOCUMENTS

EP 0344397 A2 12/1989
JP S54150156 U 10/1979
(Continued)

OTHER PUBLICATIONS

English Machine Translation of JPS54150156U dated Oct. 18, 1979.
English Machine Translation of JPH0424447A dated Jan. 28, 1992.
English Machine Translation of JPH0926226A dated Jan. 28, 1997.
(Continued)

*Primary Examiner* — Edward F Landrum
*Assistant Examiner* — Daniel C Comings
(74) *Attorney, Agent, or Firm* — King & Schickli, PLLC

(57) ABSTRACT

A test chamber for conditioning air has a temperature-insulated test space sealable against an environment for receiving test materials and a temperature control device for controlling the temperature of the test space, a temperature ranging from −20° C. to +180° C. in temperature being able to be realized within the test space by means of the temperature control device, said temperature control device comprising a cooling device having a cooling cycle having a refrigerant, a heat transmitter, a compressor, a condenser and an expanding element, the cooling cycle comprising an internal heat transmitter, the internal heat transmitter being connected to a high-pressure side of the cooling cycle upstream of the expanding element and downstream of the condenser in a flow direction, said refrigerant being able to cooled by means of the internal heat transmitter which is coupled to an adjustable supplementary refrigeration of the cooling device.

23 Claims, 3 Drawing Sheets

(51) Int. Cl.
*F25B 40/02* (2006.01)
*F25B 15/00* (2006.01)
*F25B 21/02* (2006.01)

(52) U.S. Cl.
CPC .......... *F25B 27/02* (2013.01); *F25B 2400/01* (2013.01); *F25B 2400/054* (2013.01); *F25B 2400/12* (2013.01); *F25B 2600/2501* (2013.01)

(56) References Cited

FOREIGN PATENT DOCUMENTS

| | | |
|---|---|---|
| JP | H0424447 A | 1/1992 |
| JP | H0926226 A | 1/1997 |
| JP | 2007183126 A | 7/2007 |
| JP | 2008075919 A | 4/2008 |
| JP | 2010249356 A | 11/2010 |
| JP | 2011149566 A | 8/2011 |
| JP | 2012088022 A | 5/2012 |
| JP | 2012247104 A | 12/2012 |
| JP | 2012247156 A | 12/2012 |
| JP | 2014074557 A | 4/2014 |
| KR | 100984280 B1 | 9/2010 |
| WO | WO2006062860 A2 | 6/2006 |

OTHER PUBLICATIONS

English Machine Translation of JP2007183126A dated Jul. 19, 2007.
English Machine Translation of JP2008075919A dated Apr. 3, 2008.
English Machine Translation of JP2010249356A dated Nov. 4, 2010.
English Machine Translation of JP2011149566A dated Aug. 4, 2011.
English Machine Translation of JP2012088022A dated May 10, 2012.
English Machine Translation of JP2012247104A dated Dec. 13, 2012.
English Machine Translation of JP2012247156A dated Dec. 13, 2012.
English Machine Translation of JP2014074557A dated Apr. 24, 2014.
English Machine Translation of KR100984280B1 dated Sep. 30, 2010.

\* cited by examiner

TEST CHAMBER WITH TEMPERATURE CONTROL DEVICE

TECHNICAL FIELD

The invention relates to a test chamber for conditioning air, comprising a temperature-insulated test space sealable against an environment for receiving test materials and a temperature control device for controlling the temperature of the test space, a temperature ranging from −20° C. to +180° C. in temperature being able to be realized within the test space by means of the temperature control device, said temperature control device comprising a cooling device having a cooling cycle having a refrigerant, a heat transmitter, a compressor, a condenser and an expanding element.

Such test chambers are commonly used for testing physical and/or chemical properties of objects, in particular devices. Therefore, temperature test chambers or climate test chambers are known within which temperatures ranging from −50° C. to +180° C. can be set. In climate test chambers, desired climate conditions can be additionally set to which the device or rather test materials will be exposed for a defined period of time. Such test chambers are regularly or partially realized as a mobile apparatus which are merely connected to a building using required supply lines and comprise all necessary structural components for controlling the temperature and conditioning. A temperature of a test space, which receives the test materials to be tested, is regularly controlled in an air circulation duct within the test space. The air circulation duct forms an air treatment space in the test space in which heat exchangers for heating or cooling the air flowing through the air circulation duct or the test space, respectively, are arranged. For this purpose, a fan or a ventilator suctions the air present in the test space and directs it in the air circulation duct to the corresponding heat exchangers. The test materials can thus be controlled in temperature or even be exposed to a defined change in temperature. During a test interval, a temperature can repeatedly alternate between a temperature maximum and a temperature minimum of the test chamber.

BACKGROUND

The refrigerant circulating in the cooling cycle has to be realized in such a manner that it can be used in the cooling cycle within the above-mentioned temperature range. Due to legal provisions, the refrigerant must not substantially contribute to the ozone depletion in the atmosphere or to global warming. Thus, no fluorinated gases or chlorinated materials may be used as refrigerants, which is why natural refrigerants or rather gases are eligible instead. Furthermore, the refrigerant should not be flammable so that filling, shipping or operating the test chamber is not complicated due to security measures which have to be possibly met. Producing a cooling cycle also becomes more expensive when using a flammable refrigerant in consequence of required constructive measures appertaining thereto. Being flammable is understood in this context to mean the characteristic of the refrigerant to react with ambient oxygen under release of heat. A refrigerant is flammable in particular when it falls under fire class C of the European Standard EN 2 as well as under DIN 378 classes A2, A2L and A3.

Furthermore, a refrigerant should comprise a fairly low $CO_2$ equivalent, i.e. a fairly low greenhouse potential or global warming potential (GWP) should be as low as possible in order to prevent indirectly damaging the environment via the refrigerant upon release. The GWP indicates how much a predetermined mass of a greenhouse gas contributes to global warming, with carbon dioxide serving as a comparable figure. The value describes the average warming effect over a predetermined period of time, 20 years having been stipulated for comparison. For defining the relative $CO_2$ equivalent or GWP, the Fifth Assessment Report of the Intergovernmental Panel on Climate Change (IPCC), Assessment Report, Appendix 8.A, Table 8.A is referred to.

A disadvantage of refrigerants having a low GWP, for example <2500, is that these refrigerants comprise a partially significantly reduced refrigerating capacity in comparison to refrigerants having a comparatively high GWP in the temperature ranges relevant for test chambers.

SUMMARY

The object of the invention at hand is therefore to propose a test chamber with which temperatures of at least −30° C. can be reached and which should be able to be operated using environmentally friendly refrigerants.

The object is attained by a test chamber having a temperature-insulated test space sealable against an environment for receiving test materials and a temperature control device for controlling the temperature of the test space, a temperature ranging from −20° C. to +180° C. in temperature being able to be realized within the test space by means of the temperature control device, said temperature control device comprising a cooling device having a cooling cycle having a refrigerant, a heat transmitter, a compressor, a condenser and an expanding element, the cooling cycle comprising an internal heat transmitter, said internal heat transmitter being connected to a high-pressure side of the cooling cycle upstream of the expanding element and downstream of the condenser in a flow direction, said refrigerant being able to cooled by means of the internal heat transmitter which is coupled to an adjustable supplementary refrigeration of the cooling device.

In the test chamber according to the invention, a temperature exchange with an environment of the test space is mostly prevented via a temperature isolation of lateral walls, floor walls and ceiling walls. The heat transmitter is connected to the cooling cycle or is integrated therein so that the refrigerant circulating in the cooling cycle flows through the heat transmitter. The heat transmitter of the cooling cycle can be arranged within the test space or in an air treatment space of the test space or alternatively be coupled to another cooling cycle of the cooling device should the cooling device comprise two cascaded cooling cycles. The heat transmitter serves as a condenser for the other cooling cycle. The cooling device further comprises the compressor as well as the condenser for the compressed refrigerant, said condenser being arranged downstream of the compressor in the flow direction of the refrigerant. The compressed refrigerant, which is highly pressurized after having been compressed and is essentially gaseous, condenses in the condenser and is then essentially liquid. The liquid refrigerant continues flowing via the expanding element, where it in turn becomes gaseous when expanding following a drop in pressure. In doing so, it flows through the heat transmitter, which is thus cooled. Subsequently, the gaseous refrigerant is suctioned again by the compressor and compressed. An expanding element is understood to be at least an expansion valve, a throttle, a throttle valve or a different, suitable constriction of a fluid line.

In the present invention, it is intended to connect the internal heat transmitter on a high-pressure side of the cooling cycle upstream of the expanding element and downstream of the condenser in a flow direction or to integrate it into the cooling cycle. Accordingly, the refrigerant liquefied by the condenser flows from the condenser through the internal heat transmitter to the expanding element. In doing so, the refrigerant can be cooled by means of the internal heat transmitter. This occurs by the internal heat transmitter being coupled to an adjustable supplementary refrigeration of the cooling device. The adjustable supplementary refrigeration can be any possible type of cooling device which enables any further cooling or undercooling of the refrigerant by means of the internal heat transmitter. Through this, it becomes possible in particular to compensate the reduced refrigerating capacity of the refrigerant having a comparatively low GWP. Since the supplementary refrigeration can be adjusted, the supplementary refrigeration can be adjusted to an undercooling of the refrigerant as required. Since the undercooling is subject to fluctuations in capacity in regard of a refrigerating capacity depending on the type of undercooling, it is possible to also adjust these fluctuations in capacity by controlling the supplementary refrigeration to a demand of the cooling device so that no undesired fluctuations in temperature or deviations in temperature from a predetermined temperature of the refrigerant occur. Overall, it thus becomes possible to compensate a reduced refrigerating capacity of the test chamber when operated using an environmentally friendly refrigerant.

A temperature ranging from −60° C. to +180° C., preferably −80° C. to +180° C., in temperature can be realized within the test space by means of the temperature control device. A temperature ranging from −30° C. to +180° C., preferably −42° C. to +180° C., at the least is intended.

It is essential that a temperature ranging from >+60° C. to +180° C. in temperature within the test space can be reduced by means of the temperature control device. The refrigerant is heavily heated in the heat transmitter via the comparatively high temperature in the test space, which is why the cooling cycle can be technically adjusted to a refrigerant heated to this temperature range in regard of its construction, at least on a low-pressure side of the cooling cycle. Such a heated refrigerant can otherwise no longer be ideally used on the high-pressure side of the cooling cycle.

The refrigerant can comprise a relative $CO_2$ equivalent of <2500, preferably <500, particularly preferably <100, based on 20 years and can thus be only slightly harmful to the environment. Furthermore, the refrigerant can also not be flammable, whereby it becomes possible to realize the test chamber and in particular the cooling cycle less expensively since no particular safety measures regarding the flammability of the refrigerant need be considered. The refrigerant then cannot be allocated to fire class C and/or the refrigerant safety group A1. Moreover, shipping or transporting the test chamber is facilitated since the test chamber can be filled with the refrigerant prior to a transport, independently of the type of transportation. With flammable refrigerants, the test chamber can potentially only be filled in the scope of a launch at the place of installation. Furthermore, it is possible to use the non-flammable refrigerant with ignition sources in the test space. Sensors for detecting an ignitable atmosphere in the area of the heat transmitter in the test space are unnecessary. Such sensors are commonly not thermally stable.

In one embodiment of the test chamber, the heat transmitter can be arranged in a test space. The heat transmitter can then also be arranged in an air conditioning space of the test space so that air circulated by a fan can come into contact with the heat transmitter. It thus becomes possible to directly cool an amount of circulated air from the test space via the heat transmitter in the test space by means of the cooling device. The test chamber can then comprise the cooling cycle as a single, individual cooling cycle. The cooling cycle is then directly connected to the test space.

In another embodiment of the test chamber, the heat transmitter can form a cascading heat transmitter for another cooling cycle of the cooling device. Accordingly, the test chamber can then comprise at least two cooling cycles, the cooling cycle realizing a first stage of the cooling device and another cooling cycle, which is directly connected to the test space, realizing a second stage of the cooling device. The cascading heat transmitter or the heat transmitter, respectively, then also serves as a condenser for the other cooling cycle. In this embodiment of test chamber, it is then possible to realize particularly low temperatures in the test space.

The other cooling cycle can comprise another refrigerant, another compressor, another heat transmitter, another condenser and another expanding element, said other heat transmitter being able to be arranged in the test space, said other cooling cycle being able to be coupled to the cascading heat transmitter of the cooling cycle by means of the other condenser. The cooling device then comprises two cycles which are switched consecutively and realize as a so-called cold cascade.

The temperature control device can comprise a heating device having a heater and a heating heat transmitter in the test space. The heating device can be an electric resistance heating, for example, which heats the heating heat transmitter in such a manner that a rise in temperature in the test space becomes possible via the heating heat transmitter. If the heat transmitter and the heating heat transmitter are to be able to be systematically controlled by means of a control device for cooling or heating the air circulated in the test space, a temperature ranging in the temperatures described above can be realized within the test space by means of the temperature control device. In this context, a temporal temperature stability of ±1 K, preferably ±0.3 K to ±0.5 K, can be realized in the test space during a testing interval, independently of the test materials or an operating condition of the test materials. In this context, a testing interval is understood to be a period of time of an entire testing period in which the test materials are subjected to an essentially stable temperature or climatic condition. The heating heat transmitter can be combined with the heat transmitter of the cooling cycle in such a manner that a shared heat transmitter is formed through which a refrigerant can flow and which comprises heating elements of an electrical resistance heater. The condenser can be realized having an air cooler or water cooler or another different cooling liquid. Generally, the condenser can be cooled using any suitable fluid. It is essential that the thermal load occurring at the condenser is dissipated via the air cooler or water cooler such that the refrigerant can condensate in such a manner that it becomes completely liquefied.

Furthermore, a pressure equalization device can be arranged in the cooling cycle for the refrigerant, a pressure of <40 bars, preferably <25 bars, being able to be realized in the cooling cycle when a temperature of the refrigerant is consistently realized at 20° C. in the cooling cycle. Provided that another cooling cycle is present, this cooling cycle can also comprise such a pressure equalization device. Since comparatively large differences in temperature can be present in the cooling cycle, it is particularly advantageous if the pressure equalization device can compensate these differences. Thus, very large fluctuations in temperature and consequently a change in volume of the refrigerant can be compensated in dependence of the corresponding expansion coefficient of the refrigerant via the pressure equalization device. The pressure equalization device can be a refrigerant reservoir, for example, which is connected to a low-pressure side of the cooling cycle.

In particular, it can be intended that the pressure equalization device can be realized such that the temperature control device is intrinsically safe when without current, i.e. no standstill cooling of the refrigerant is required. It is also possible to already completely fill the cooling cycle prior to transporting the test chamber so as to be ready for operation.

Furthermore, the internal heat transmitter can be coupled to an adjustable external supplementary cooling and/or an adjustable internal supplementary cooling of the cooling cycle. An external supplementary cooling is understood to be a supplementary cooling in which energy is applied for cooling the internal heat transmitter from a device independent of the cooling cycle. An internal supplementary cooling is understood to be a supplementary cooling in which energy or refrigerating capacity of the cooling cycle is used for cooling the internal heat transmitter via a device integrated into the cooling cycle. In the internal supplementary cooling of the cooling cycle, consequently, no additional energy, with the exception of the compressor, heat transmitter and condenser, is externally supplied to the cooling cycle as in comparison to the external supplementary cooling.

The adjustable external supplementary cooling can be realized as a resupply of a freezing stage of the cooling device or as an external cooling water piping, said resupply or cooling water piping being able to be connected to the internal heat transmitter. In a simple embodiment, the external supplementary cooling is a cooling water piping merely coupled to the internal heat transmitter, said cooling water piping being cooled by another external, in this instance, cooling device if required. Provided that the test chamber comprises at least two cooling cycles, a second stage or rather the freezing stage of the cooling device or rather another cooling cycle of the cooling device can be channeled via the internal heat transmitter or be connected thereto.

Alternatively, the adjustable external supplementary cooling can be realized as a Peltier element or a heating tube. The internal heating transmitter can then be formed from a pipe section of the cooling cycle, for example, to which Peltier elements or heating tubes are fastened.

According to another embodiment, the adjustable internal supplementary cooling can be realized as an absorption chiller which can be connected to the internal heat transmitter, said absorption chiller being able to be driven using waste heat of the compressor. The waste heat of the compressor can be dissipated directly from the compressor, e.g. from a compressor or a tube section of the high-pressure side of the cooling cycle, to the condenser. A cooling cycle of the absorption chiller can then also be channeled through the internal heat transmitter.

According to an advantageous embodiment, the adjustable internal supplementary cooling can be realized as a resupply of the cooling cycle arranged downstream of the expanding element in a flow direction, said resupply being able to be connected to the internal heat transmitter. A pipe section of the high-pressure side of the cooling cycle can, for example, be resupplied entirely or in the type of a bypass downstream of the expanding element or be channeled through the internal heat transmitter so that the expanding element itself cools a pipe section of the cooling cycle upstream of the expanding element in a flow direction.

According to a particularly advantageous embodiment, a first bypass having at least one adjustable second expanding element can be realized in the cooling cycle, said first bypass being able to be connected to the cooling cycle upstream of the internal heat transmitter and downstream of the condenser in a flow direction, said first bypass being able to be realized as an adjustable internal supplementary cooling. The refrigerant can then be at least partially deflected in the first bypass upstream of the expanding organ in the flow direction, the refrigerant decompressing and thus cooling down by means of the second expanding element. This refrigerant can then be used for cooling the refrigerant upstream of the expanding element. The thus realized internal supplementary cooling can be controlled in particular via the second expanding element so that the internal supplementary cooling can always be adjusted to the operating requirements of the cooling device.

Furthermore, the internal heat transmitter can be connected to a low-pressure side of the cooling cycle upstream of the compressor and downstream of the heat transmitter in a flow direction, said first bypass being able to form a back-injection device for refrigerants, said first bypass being able to be connected to a low-pressure side of the internal heat transmitter via a back-injection valve, a refrigerant being able to be supplied to the back-injection valve from the adjustable second expanding element. Accordingly, the refrigerant guided from the heat transmitter can be supplied into the internal heat transmitter on the low-pressure side, the refrigerant heated in the heat transmitter being able to be cooled from the first bypass by adding a refrigerant having a comparatively low temperature. The refrigerant is added from the first bypass via the back-injection valve, which can be realized as a simple T-piece in a pipe section of the cooling cycle, for example. Controlling the second expanding element is particularly advantageous in this instance since a temperature can be set ever lower on the low-pressure side of the internal heat transmitter via the back-injection device than it could be on the high-pressure side of the internal heat transmitter. This can be particularly advantageous if there are temperatures of >60° C. in a test space and the refrigerant from the heat transmitter is accordingly heated.

The back-injection valve can be connected to the internal heat transmitter in the flow direction or rather the flow direction of a suction gas mass flow after ¼ to ½, preferably ⅓, of a heat-transmitting section of the internal heat transmitter. For this purpose, the internal heat transmitter can be realized as a type of undercooling section.

Optionally, a low-pressure side of the internal heat transmitter can be connected to the first bypass downstream of the adjustable second expanding element in a flow direction, a refrigerant being able to be supplied to the internal heat transmitter from the adjustable second expanding element, said internal heat transmitter being able to be connected to a low-pressure side of the cooling cycle upstream of the compressor and downstream of the heat transmitter in a flow direction, a refrigerant being able to be supplied to the compressor from the low-pressure side of the internal heat transmitter. The refrigerant heated by the heat transmitter is consequently not guided directly through the internal heat transmitter but rather only the refrigerant cooled by the first bypass. After the refrigerant cooled via the second expanding element or rather reduced in temperature has been channeled through the internal heat transmitter, the refrigerant can be supplied to a pipe section of the cooling cycle which leads from the heat transmitter to the compressor. A refrigerating capacity of the internal heat transmitter can consequently be controlled even more precisely.

Furthermore, a second bypass having at least a third expanding element can be realized in the cooling cycle, said second bypass bridging the expanding element downstream of the condenser and upstream of the internal heat transmitter in a flow direction, a refrigerant being dosed via the third expanding element in such a manner that a suction gas temperature and/or a suction gas pressure of the refrigerant can be controlled on a low-pressure side of the cooling cycle upstream of the compressor. Through this, it can be prevented, amongst other things, that the compressor potentially overheats and thus becomes damaged. Consequently, a gaseous refrigerant present upstream of the compressor via the second bypass by actuating the third expanding element can be cooled by adding still liquid refrigerant. The third expanding element can be actuated via a control device which is coupled to a pressure sensor and/or a temperature sensor in the cooling cycle upstream of the compressor. It is particularly advantageous if a suction gas temperature of ≤30° C. can be set via the second bypass. The refrigerant can also be dosed such that an operating period of the compressor can be controlled. Generally, it is disadvantageous if the compressor is often turned on and off. A service life of a compressor can be prolonged if it remains in operation over long periods at a time. A refrigerant can be guided past the expanding element or the condenser via the second bypass in order to delay the compressor from automatically shutting off and to prolong an operating period of the compressor, for example.

Another bypass having at least another expanding element can be realized in the cooling cycle, said other bypass being able to bridge the compressor downstream of the compressor and upstream of the condenser in a flow direction in such a manner that a suction gas temperature and/or a suction gas pressure of the refrigerant can be controlled on a low-pressure side of the cooling cycle upstream of the compressor and/or that a difference in pressure between the high-pressure side and the low-pressure side of the cooling cycle can be compensated. The other bypass can be complementarily provided with an adjustable or controllable valve, e.g. a magnetic valve. Through the connection between the high-pressure side and the low-pressure side via the other expanding element, it can be ensured that the gaseous refrigerant compressed in this manner gradually flows to the low-pressure side of the cooling cycle from the high-pressure side when the installation comes to a standstill. Thus, it is ensured even in closed expanding elements that pressure is gradually compensated between the high-pressure side and the low-pressure side. A cross section of the other expanding element can be measured such that an overflow of the refrigerant from the high-pressure side to the low-pressure side only minimally influences a normal operation of the cooling device. Nevertheless, it can be intended that a gaseous refrigerant upstream of the compressor is cooled by adding the liquid refrigerant via the other bypass.

The internal heat transmitter can be realized as an undercooling section or a heat transmitter, in particular a plate heat exchanger. The undercooling section can be realized by only two pipe sections of the cooling cycle arranged next to each other.

The expanding element can comprise a throttle and a magnetic valve, a refrigerant being able to be dosed via said throttle and said magnetic valve. The throttle can be an adjustable valve or capillary via which a refrigerant can be guided by means of the magnetic valve. The magnetic valve can be actuated by means of a control device.

Furthermore, the temperature control device can comprise a control device having at least one pressure sensor and/or at least one temperature sensor in the cooling cycle, magnetic valves being able to be actuated by means of the control device in dependence of a measured temperature or a pressure. The control device can comprise means for processing data which process data sets from sensors and control the magnetic valves. Regulating a function of the cooling device can also be adjusted to the used refrigerant, via a corresponding computer program, for example. Furthermore, the control device can indicate an operation disturbance and initiate shutting off the test chamber, if necessary, in order to protect the test chamber or the test materials from becoming damaged via critical or undesired operating conditions of the test chamber.

BRIEF DESCRIPTION OF THE DRAWING FIGURES

In the following, preferred embodiments of the invention are further described with reference to the enclosed drawings.

In the figures.

DETAILED DESCRIPTION

Figure 1:
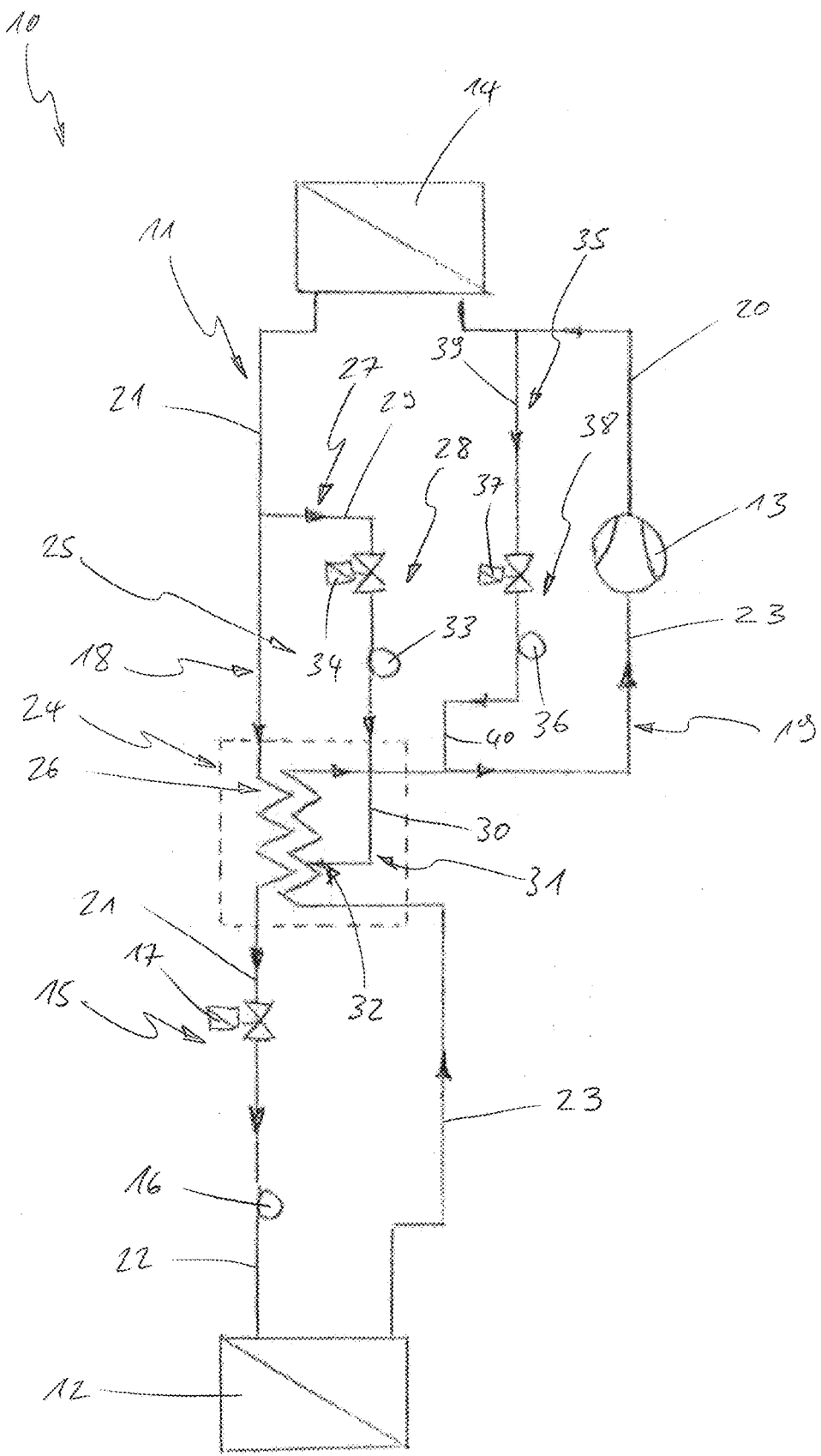
FIG. 1 shows a schematic view of a first embodiment of a cooling device.

FIG. 1 illustrates a schematic view of a cooling device 10 having a cooling cycle 11 within which a refrigerant can circulate. The refrigerant comprises a relative $CO_2$ equivalent of <2500 based on 20 years. Furthermore, the cooling device 10 comprises a heat transmitter 12, which is arranged in a test space not further shown here or connected to another cooling cycle not further shown here, a compressor 13, a condenser 14 and an expanding element 15. The expanding element 15 is formed from a throttle 16 and a magnetic valve 17. The cooling cycle 11 comprises a high-pressure side 18, which extends from the compressor 13 to the expanding element 15 in a flow direction of the refrigerant, as well as a low-pressure side 19, which extends from the expanding element 15 to the compressor 13. In a tube section 20 from the compressor 13 to the condenser 14, the refrigerant is gaseous and comprises a comparatively high temperature. The refrigerant compressed by the compressor 13 flows to the condenser 14 in the cooling cycle 11, said gaseous refrigerant being liquefied in the condenser 14. In the flow direction of the refrigerant, the heat transmitter 12 follows after the condenser 14 in the cooling cycle 11, said refrigerant being present in a liquid state accordingly in a tube section 21 of the cooling cycle 11 between the condenser 14 and the expanding element 15. Via the refrigerant expanding downstream to the expanding element 15, the heat transmitter 12 is cooled, said refrigerant transitioning to the gaseous state in a tube section 22 between the expanding element 15 and the heat transmitter 12 and being guided via a tube section 23 from the heat transmitter 12 to the compressor 13.

In the cooling cycle 11, an internal heat transmitter 24 is further connected on the high-pressure side 18 of the cooling cycle 11 in the tube section 21. The internal heat transmitter 24 is coupled to an adjustable supplementary cooling 25. Furthermore, the internal heat exchanger 24 is realized as an undercooling section 26. Thus, the tube section 23 is guided towards the tube section 21 in sections in such a manner that heat can be transmitted between the tube sections 21 and 23.

The adjustable internal supplementary cooling 25 is formed by a first bypass 27 having an adjustable second expanding element 28, said first bypass 27 branching off of the tube section 21 in conjunction with a tube section 29 and forming a back-injection device 31 for the refrigerant in conjunction with a tube section 30 downstream of the second expanding element 28. The tube section 30 in particular is connected to the tube section 23 in the area of the undercooling section 26 by means of a back-injection valve 32. The back-injection valve 32 is connected to the undercooling section 26 after ⅓ of the length of the undercooling section 26 in the flow direction of the refrigerant. Controlling the internal supplementary cooling 25 becomes possible by the second expanding element 28 comprising a throttle 33 and a magnetic valve 34, by means of which the temperature of the refrigerant can be reduced and be added in the undercooling section 26 or the corresponding tube section 23 to the comparatively warm refrigerant flowing there. Through this, the refrigerant flowing in the tube section 21 upstream to the expanding element 15 in the undercooling section 26 is cooled. Through this so-called undercooling of the liquefied refrigerant on the high-pressure side 18, it becomes possible to compensate a reduced refrigerating capacity of the refrigerant in comparison to refrigerants having a GWP of >2500. Nevertheless, a possibly fluctuating temperature of the refrigerant flowing from the heat transmitter 12 can be compensated via controlling adding the refrigerant, in particular when temperatures of >60° C. are realized in the test space.

Furthermore, a second bypass 35 having a throttle 36 and a magnetic valve 37, which form a third expanding element 38, is arranged in the cooling cycle 11. Tube sections 39 and 40 of the second bypass 35 bridge the compressor 13 such that pressure is gradually compensated between the high-pressure side 18 and the low-pressure side 19 via the third expanding element 38 when it comes to a standstill of the compressor 13. Furthermore, a suction gas temperature and/or a suction gas pressure of the refrigerant can be adjusted on the low-pressure side 19 of the cooling cycle 11 upstream of the compressor 13 via the magnetic valve 37.

Figure 2:
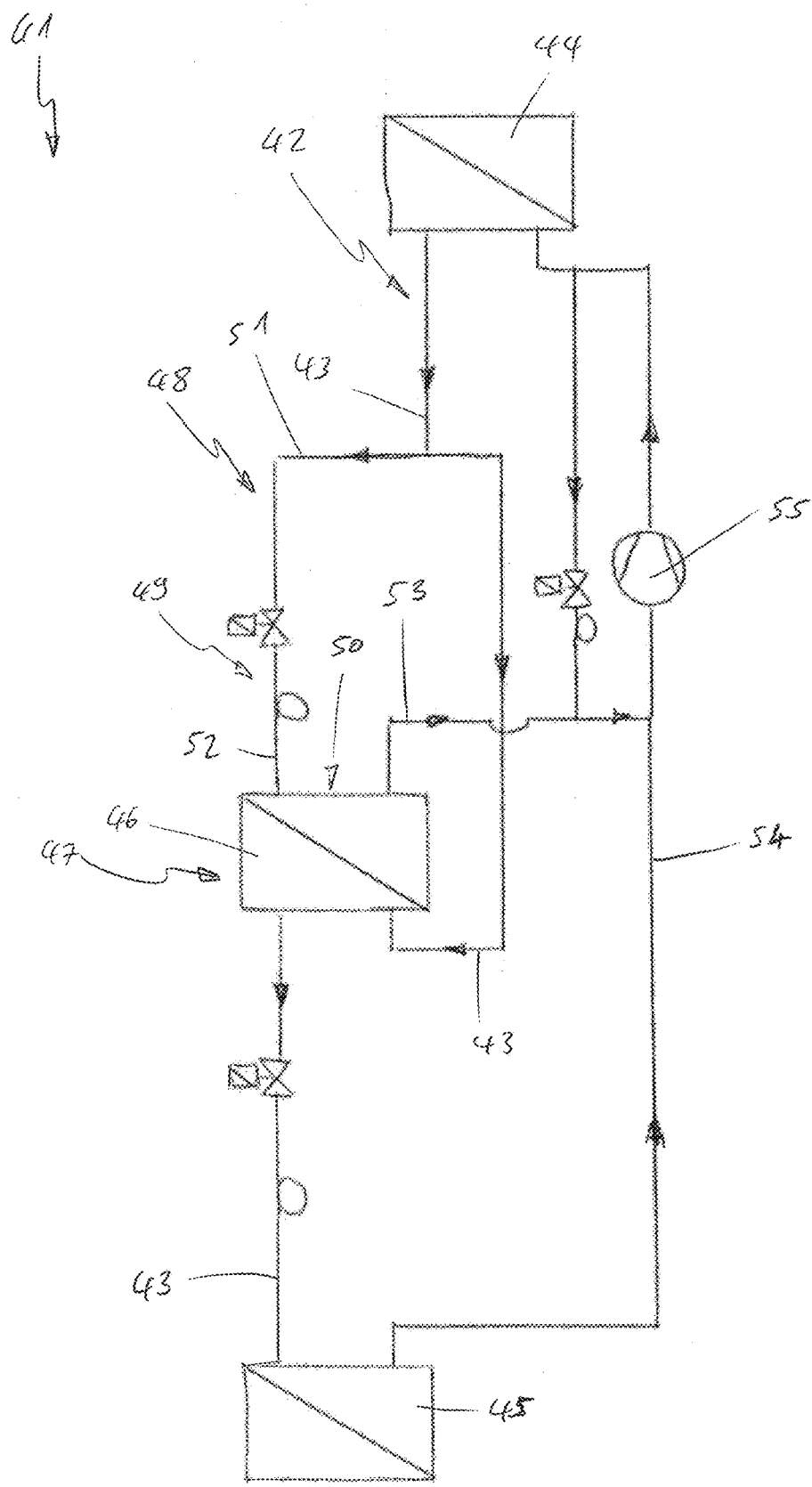
FIG. 2 shows a schematic view of a second embodiment of a cooling device.

FIG. 2 illustrates a cooling device 41 which, in comparison to the cooling device from FIG. 1, comprises a cooling cycle 42 having a tube section 43 between a condenser 44 and a heat transmitter 45 in which an internal heat transmitter 47 realized as a heat exchanger 46 is arranged. A first bypass 48 having a second expanding element 32 branches off before the heat transmitter 46 upstream of the tube section 43 and is directly connected to the heat transmitter 46 on a low-pressure side 50 of the internal heat transmitter 47. The first bypass is formed from tube sections 51 and 52, a tube section 43 opening from the low-pressure side 50 into a tube section 54 upstream of a compressor 55 in a flow direction.

Figure 3:
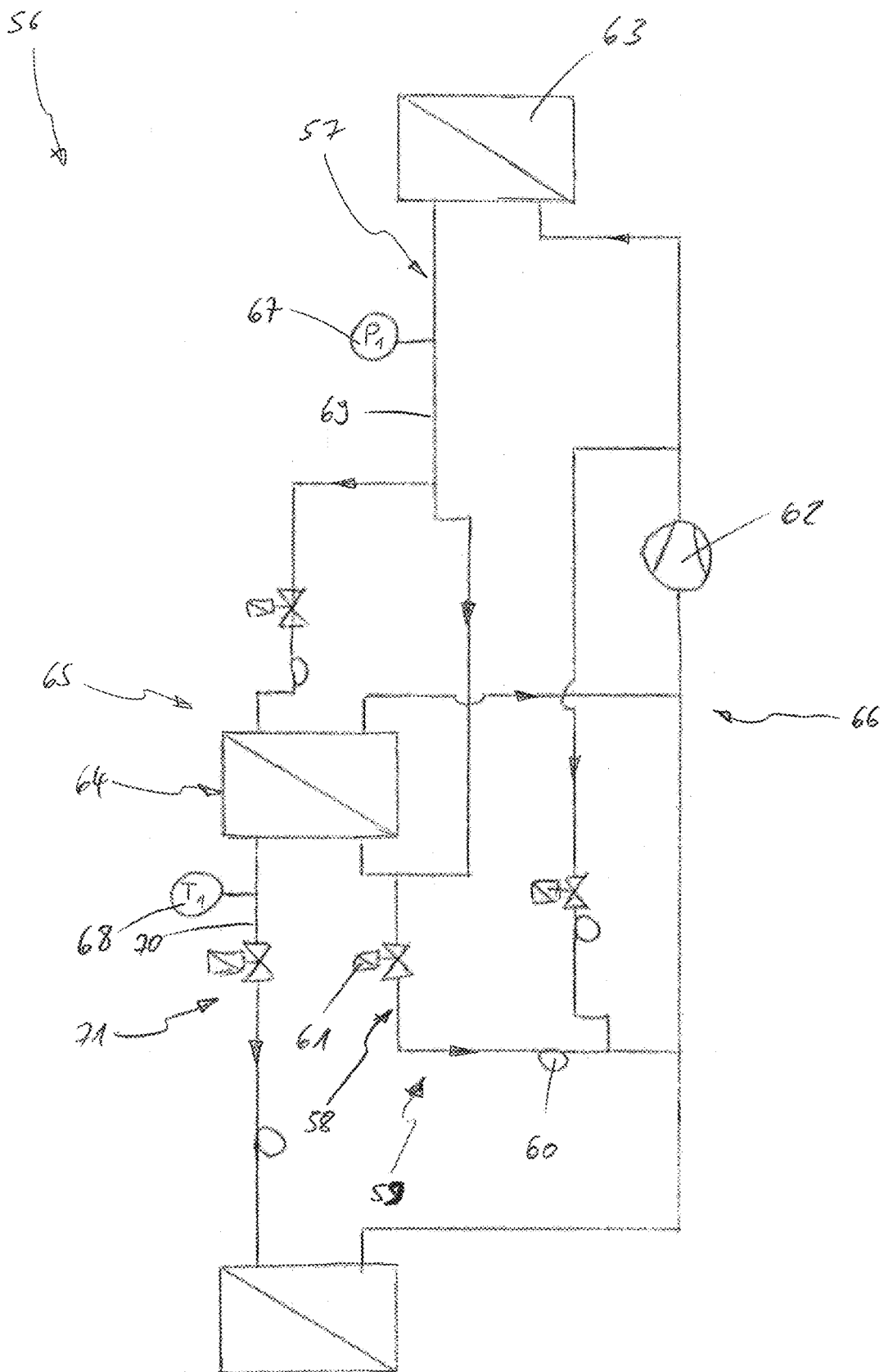
FIG. 3 shows a schematic view of a third embodiment of a cooling device.

FIG. 3 illustrates a cooling device 56 having a cooling cycle 57, another bypass 58 having another expanding element 59 being provided in this instance, as opposed to the cooling device from FIG. 2. The other expanding element 59 also comprises a throttle 60 and a magnetic valve 61. The other bypass 58 bridges a compressor 62 downstream of a condenser 63 and upstream of an internal heat transmitter 64 from a high-pressure side 65 to a low-pressure side 66 of the cooling cycle 57. The other bypass 58 can thus be used for controlling a suction gas temperature upstream of the compressor 62.

Furthermore, a pressure sensor 67 and a temperature sensor 68 are intended in the cooling cycle 57. A refrigerant pressure can be measured in a tube section 69 downstream of the condenser using the pressure sensor 67 and a refrigerant temperature can be measured directly in a tube section 70 upstream of an expanding element 71 using the temperature sensor 68. It is intended in particular to control a temperature of the refrigerant in dependence of a pressure by means of a control device not further shown here.

The invention claimed is:

1. A test chamber for conditioning air, comprising a temperature-insulated test space sealable against an environment for receiving test materials and a temperature control device for controlling the temperature of the test space, a temperature ranging from 20° C. to +180° C. in temperature being able to be realized within the test space by means of the temperature control device, said temperature control device comprising a cooling device (10, 41, 56) having a cooling cycle (11, 42, 57) having a refrigerant, a heat transmitter (12, 45), a compressor (13, 55, 62), a condenser (14, 44, 63) and an expanding element (15, 71), characterized in that the cooling cycle comprises an internal heat transmitter (24, 47, 64), the internal heat transmitter being connected to a high-pressure side (18, 65) of the cooling cycle upstream of the expanding element and downstream of the condenser in a flow direction, said refrigerant being able to be cooled by means of the internal heat transmitter which is coupled to an adjustable supplementary refrigeration of the cooling device.

2. The test chamber according to claim 1, characterized in that a temperature ranging from 50° C. to +180° C., preferably from 80° C. to +180° C., in temperature, can be realized within the test space by means of the temperature control device.

3. The test chamber according to claim 1, characterized in that a temperature ranging from +60° C. to +180° C. can be reduced from this temperature within the test space by means of the temperature control device.

4. The test chamber according to claim 1, characterized in that the refrigerant comprises a relative CO2 equivalent of <2500, preferably <500, particularly preferably <100, based on 20 years, said refrigerant being inflammable.

5. The test chamber according to claim 1, characterized in that the heat transmitter (12, 45) is arranged in the test space.

6. The test chamber according to claim 1, characterized in that the heat transmitter (12, 45) forms a cascading heat transmitter for an-other cooling cycle of the cooling device (10, 41, 56).

7. The test chamber according to claim 6, characterized in that the other cooling cycle comprises another refrigerant, another compressor, another heat transmitter, another condenser and another expanding element, said other heat transmitter being arranged in the test space, said other cooling cycle being coupled to the cascading heat transmitter of the cooling cycle (11, 42, 57) by means of the other condenser.

8. The test chamber according to claim 1, characterized in that the temperature control device comprises a heating device having a heater and a heating heat transmitter in the test space.

9. The test chamber according to claim 1, characterized in that the condenser (14, 44, 63) is realized having air cooler or water cooler or a different cooling liquid.

10. The test chamber according to claim 1, characterized in that the internal heat transmitter (12, 45) is further coupled to an adjustable internal supplementary refrigeration (25) of the cooling cycle (11, 42, 57).

11. The test chamber according to claim 10, characterized in that the adjustable external supplementary refrigeration is realized as a re-supply of a freezing stage of the cooling device (10, 41, 56) or as an external cooling water pipe, said resupply or cooling water piping being connected to the internal heat transmitter (24, 47, 64).

12. The test chamber according to claim 10, characterized in that the adjustable external supplementary refrigeration is realized as a Peltier element or a heating tube.

13. The test chamber according to claim 10, characterized in that the adjustable internal supplementary refrigeration is realized as an ab-sorption chiller which is connected to the internal heat transmitter (24, 47, 64), said absorption chiller being able to be driven by waste heat of the compressor (13, 55, 62).

14. The test chamber according to claim 10, characterized in that the adjustable internal supplementary refrigeration (25) is realized as a resupply of the cooling cycle (11, 42, 57) arranged downstream of the expanding element (15, 71) in a flow direction, said resupply being connected to the internal heat transmitter (24, 47, 64).

15. The test chamber according to claim 10, characterized in that a first bypass (27, 48) having at least one adjustable second expanding element (28, 49) is realized in the cooling cycle (11, 42, 57), said first bypass being connected to the cooling cycle upstream of the internal heat transmitter (24, 47, 64) and downstream of the condenser (14, 44, 63) in a flow direction, said first bypass forming an adjustable internal supplementary refrigeration (25).

16. The test chamber according to claim 15, characterized in that the internal heat transmitter (24) is connected to a low-pressure side (19) of the cooling cycle (11) upstream of the compressor (13) and down-stream of the heat transmitter (12) in a flow direction, the first bypass (27) forming a back-injection device (31) for refrigerants, said first by-pass being connected to a low-pressure side (50) of the internal heat transmitter via a back-injection valve (32), a refrigerant being able to be supplied to the back-injection valve from the adjustable second expanding element (28).

17. The test chamber according to claim 16, characterized in that the back-injection valve (32) is connected to the heat transmitter (24) in the flow direction after ¼ to ½, preferably ⅓, of a heat-transmitting section (26) of the internal heat transmitter (24).

18. The test chamber according to claim 15, characterized in that a low-pressure side (50) of the internal heat transmitter (24, 47, 64) is connected to the first bypass (27) downstream of the adjustable second expanding element (28, 49) in a flow direction, a refrigerant being able to be supplied to the internal heat transmitter from the adjustable second expanding element, said internal heat transmitter being connected to a low-pressure side (19, 66) of the cooling cycle (11, 42, 57) upstream of the compressor (13, 55, 62) and downstream of the heat transmitter (12, 45) in a flow direction, a refrigerant being able to be supplied to the compressor from the low-pressure side (50) of the internal heat transmit-ter.

19. The test chamber according to claim 18, characterized in that a second bypass (35) having at least one third expanding element (38) is formed in the cooling cycle (11, 42, 57), said second bypass bridging the expanding element (15, 71) downstream of the condenser (14, 44, 63) and upstream of the internal heat transmitter in flow direction, a refrigerant being able to be dosed via the third expanding element in such a manner that a suction gas temperature and/or a suction gas pressure of the refrigerant can be adjusted on a low-pressure side (19, 66) of the cooling cycle upstream of the compressor (13, 55, 62).

20. The test chamber according to claim 1, characterized in that another bypass (58) having at least one other expanding element (59) is realized in the cooling cycle (11, 42, 57), said other bypass bridging the compressor (13, 55, 62) downstream of the compressor and upstream of the condenser (14, 44, 63) in the flow direction in such a manner that a suction gas temperature and/or a suction gas pressure of the refrigerant can be adjusted on a low-pressure side (19, 66) of the cooling cycle up-stream of the compressor and that a difference in pressure between the high-pressure side (18, 65) and a low-pressure side of the cooling cycle can be regulated.

21. The test chamber according to claim 1, characterized in that the internal heat transmitter (24, 47, 64) is realized as an undercooling section (26) or a heat exchanger (46), in particular a plate heat exchanger.

22. The test chamber according to claim 1, characterized in that the expanding element (15, 28, 38, 49, 59, 71) comprises a throttle (16, 33, 36, 60) and a magnetic valve (17, 34, 37, 61), a refrigerant being able to be dosed via the throttle and the magnetic valve.

23. The test chamber according to claim 22, characterized in that the temperature control device comprises a control device having at least one pressure sensor (67) and/or a temperature sensor (68) in the cooling cycle (11, 42, 57), magnetic valves (17, 34, 37, 61) being able to be actuated by means of the control device in dependence of a measured temperature or pressure.

* * * * *

UNITED STATES PATENT AND TRADEMARK OFFICE
CERTIFICATE OF CORRECTION

PATENT NO. : 10,571,169 B2
APPLICATION NO. : 15/795459
DATED : February 25, 2020
INVENTOR(S) : Christian Haack and Johannes Teichmann Page 1 of 1

It is certified that error appears in the above-identified patent and that said Letters Patent is hereby corrected as shown below:

In the Claims

Claim 1, Line 15: Please replace 20° C with -20° C

Claim 2, Line 32: Please replace 50° C with -50° C

Claim 2, Line 33: Please replace 80° C with -80° C

Signed and Sealed this
Fourth Day of August, 2020

Andrei Iancu
*Director of the United States Patent and Trademark Office*